(12) United States Patent  (10) Patent No.: US 7,989,487 B2
Welsh et al.  (45) Date of Patent: Aug. 2, 2011

(54) ESTROGEN RECEPTOR MODULATORS AND USES THEREOF

(75) Inventors: William J. Welsh, Princeton, NJ (US); Nina Ching Y. Wang, Cincinnati, OH (US); Ni Ai, Piscataway, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 12/307,565

(22) PCT Filed: Jul. 6, 2007

(86) PCT No.: PCT/US2007/072995
§ 371 (c)(1),
(2), (4) Date: Mar. 1, 2010

(87) PCT Pub. No.: WO2008/006093
PCT Pub. Date: Jan. 10, 2008

(65) Prior Publication Data
US 2010/0152271 A1   Jun. 17, 2010

Related U.S. Application Data

(60) Provisional application No. 60/818,748, filed on Jul. 6, 2006.

(51) Int. Cl.
*A61K 31/40* (2006.01)
*A61K 31/12* (2006.01)
(52) U.S. Cl. .................. 514/419; 514/675
(58) Field of Classification Search .......... 514/419, 514/679
See application file for complete search history.

(56) References Cited

U.S. PATENT DOCUMENTS

2006/0094699 A1*  5/2006  Kampen et al. ........... 514/171
2006/0111366 A1*  5/2006  Andersen et al. ........ 514/253.01

\* cited by examiner

*Primary Examiner* — Raymond Henley, III
(74) *Attorney, Agent, or Firm* — Fox Rothschild LLP

(57) ABSTRACT

A method for preventing, diagnosing, or treating a condition mediated by an estrogen receptor by administering to a patient in need thereof an effective amount of a compound of formula I, II, or a combination thereof: wherein R1, R3, R4, and R5 are independently selected from H, OH, and $OR_a$; R2 is selected from H, OH, and $(C=O)(C_{1-7})$alkyl; $R_a$ is $(C_{1-7})$alkyl or $(C=O)(C_{1-7})$alkyl; or a derivative of the compound selected from N-oxide derivatives, prodrug derivatives, protected derivatives, isomers, and mixtures of isomers of the compound; or a pharmaceutically acceptable salt or solvate of the compound or the derivative. Compounds of formula I and II and pharmaceuticals compositions thereof are also presented.

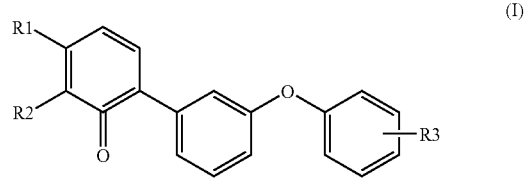

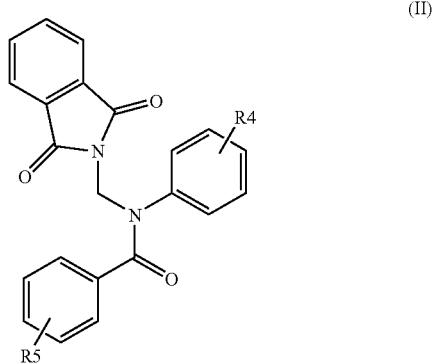

8 Claims, 3 Drawing Sheets

ESTROGEN RECEPTOR MODULATORS AND USES THEREOF

STATEMENT REGARDING FEDERALLY SPONSORED RESEARCH

The U.S. Government has a paid-up license in this invention and the right in limited circumstances to require the patent owner to license others on reasonable terms as provided for by the terms of grant TEN-13753 awarded by the United States Environmental Protection Agency.

CROSS-REFERENCE TO RELATED APPLICATIONS

This application is a National Stage filing under 35 U.S.C. §371(c) of International Application Serial No. PCT/US07/072,995 filed Jul. 6, 2007, which, in turn, claims the benefit under 35 U.S.C. §119(e) to U.S. Provisional Patent Application Ser. No. 60/818,748, which was filed on Jul. 6, 2006, the disclosures of which are incorporated herein by reference.

BACKGROUND OF THE INVENTION

Estrogens regulate a variety of physiological processes in mammals, including reproduction, bone integrity, cellular homeostasis, and cardiovascular and central nervous systems. Estrogen (17β-estradiol, E2) belongs to a family of steroid hormones that act through soluble intracellular receptors by binding to high-affinity receptors on target cells. Upon activation by estrogens, these receptors translocate to the nucleus, where they function as ligand-dependent transcription factors. Aside from a few notable exceptions, estrogenic ligands exhibit similar affinities for the two receptor subtypes ERα and ERβ.

The canonical therapy for ER-positive breast cancers employs the partial antiestrogen tamoxifen. Tamoxifen has clearly demonstrated improved prognosis in disease recurrence and overall survival in the management of early-stage breast cancer. Furthermore, recent clinical studies suggest that tamoxifen can be used prophylactically as a chemopreventive agent for hormone-dependent breast cancer.

However, drawbacks emanating from long-term treatment with tamoxifen include acquired clinical resistance and an increased risk for endometrial cancer and related uterotropic effects. Recognition of these factors has stimulated the active pursuit of alternative selective ER modulators (SERMs) that exert differential agonist and antagonistic effects in various estrogen target tissues. Raloxifene, another SERM in clinical use, was developed to improve the drug safety profile by avoiding some of the undesirable estrogen agonist actions of other SERMs.

In view of their enormous medical potential, there is a great need for fast, reliable tools to identify potential SERMs.

SUMMARY OF THE INVENTION

The present invention relates to methods for preventing, diagnosing, or treating a condition mediated by an estrogen receptor by administering to a patient in need thereof an effective amount of a compound of formula I, II, or a combination thereof:

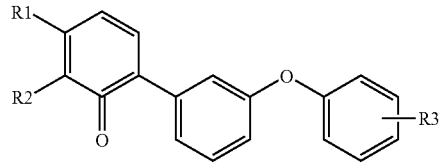
(I)

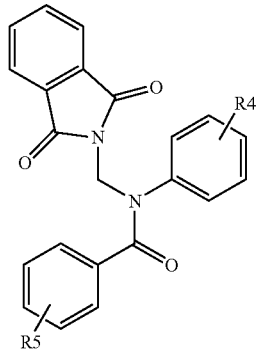
(II)

wherein R1, R3, R4, and R5 are independently selected from H, OH, and $OR_a$;
R2 is selected from H, OH, and $(C=O)(C_{1-7})$alkyl;
$R_a$ is $(C_{1-7})$alkyl or $(C=O)(C_{1-7})$alkyl; or
a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

Also provided are compounds of formula I or II:

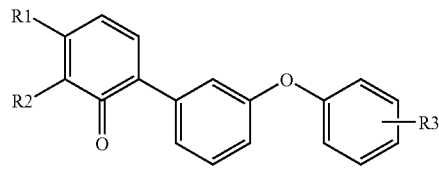
(I)

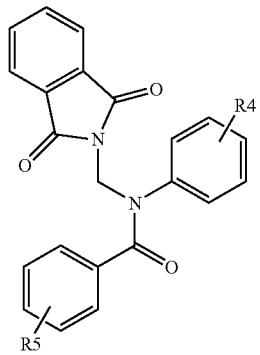
(II)

wherein R1, R3, R4, and R5 are independently selected from H, OH, and $OR_a$;
R2 is selected from H, OH, and $(C=O)(C_{1-7})$alkyl;
$R_a$ is $(C_{1-7})$alkyl or $(C=O)(C_{1-7})$alkyl; or
a derivative of the compound selected from N-oxide derivatives, prodrug derivatives, protected derivatives, isomers, and mixtures of isomers of the compound; or a pharmaceutically acceptable salt or solvate of the compound or the derivative;

provided that R3 is OH or OR$_a$ when R1 is OH and R2 is (C=O)CH$_2$CH$_3$; and

R4 is H or OR$_a$ when R5 is H.

Pharmaceutical compositions, which include an effective amount of the compound of formula I, II, or a combination thereof and a pharmaceutically acceptable carrier are also provided.

DETAILED DESCRIPTION OF THE INVENTION

Figure 1:
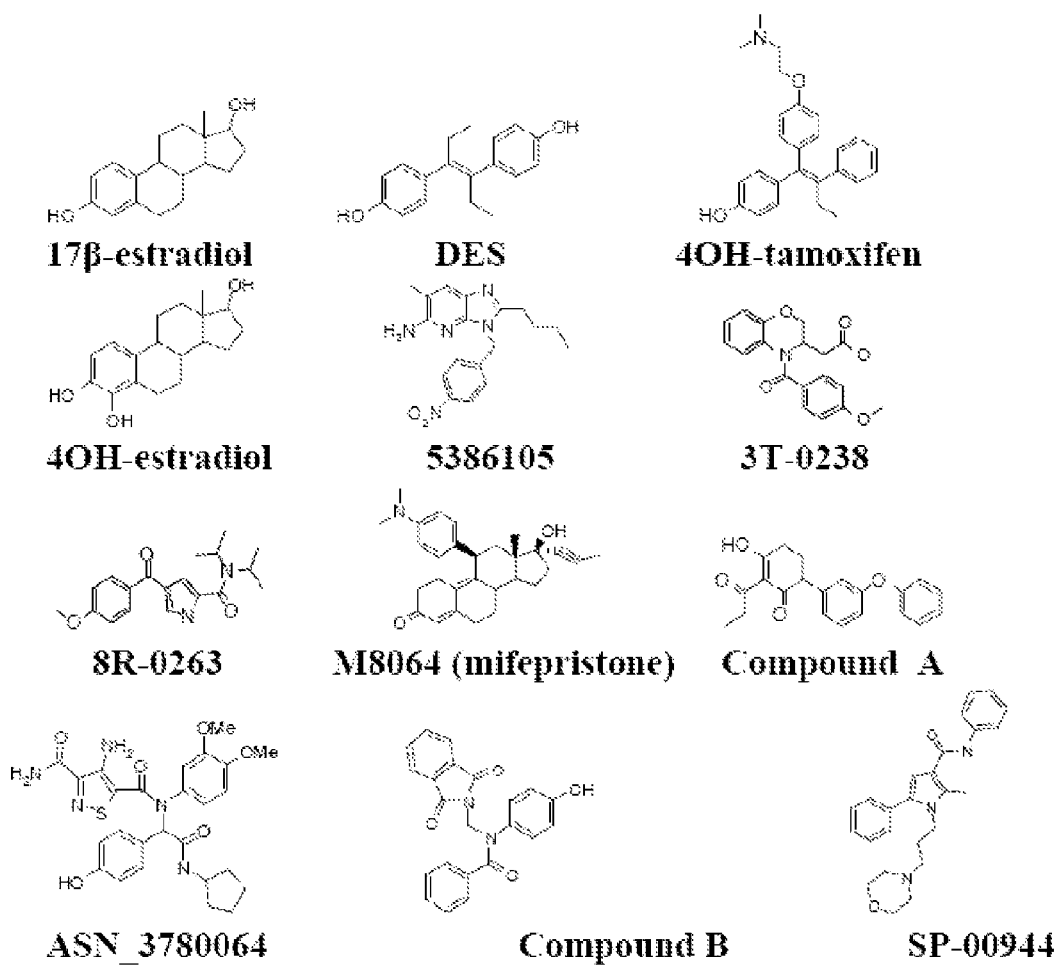
FIG. 1 illustrates the results of estrogenic activity assays on "hits" retrieved by in silico virtual screening of a chemical database.
Figure 1:
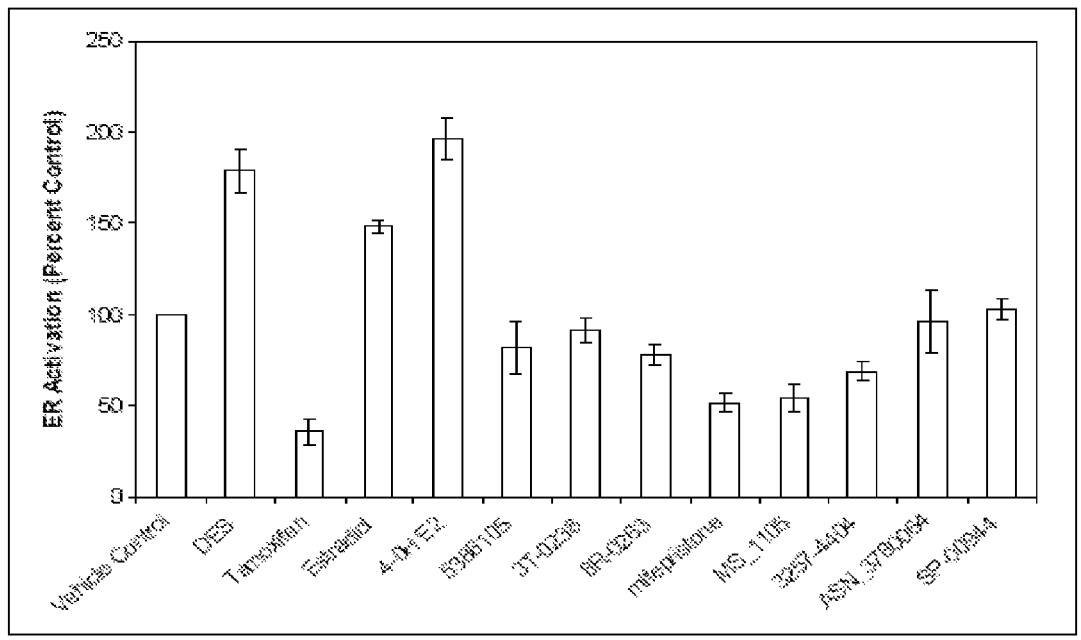

The present invention relates to methods for preventing, diagnosing, or treating a condition mediated by an estrogen receptor.

As used above, and throughout the description of the invention, the following terms, unless otherwise indicated, shall be understood to have the following meanings:

"Patient" means a mammal including a human.

"Estrogen Receptor" as defined herein refers to any protein in the nuclear receptor gene family that binds estrogen, including, but not limited to, any isoforms or deletion mutations having the characteristics just described. More particularly, the present invention relates to estrogen receptor(s) for human and non-human mammals (e.g., animals of veterinary interest such as horses, cows, sheep, and pigs, as well as household pets such as cats and dogs). Human estrogen receptors included in the present invention include the α- and β-isoforms (referred to herein as "ERα" and "ERβ") in addition to any additional isoforms as recognized by those of skill in the art.

"Estrogen Receptor Modulator" is defined herein as a compound that can act as an estrogen receptor agonist or antagonist of estrogen receptor.

"Selective Estrogen Receptor Modulator" (or "SERM") is a compound that exhibits activity as an agonist or antagonist of an estrogen receptor (e.g., ERα or ERβ) in a tissue-dependent manner. Thus, as will be apparent to those of skill in the art, compounds of the invention that function as SERMs can act as estrogen receptor agonists in some tissues (e.g., bone, brain, and/or heart) and as antagonists in other tissue types, such as the breast and/or uterine lining.

"Effective amount" means an amount of compound of the present invention effective for treating estrogen receptor mediated diseases or conditions, and thus producing the desired therapeutic effect.

"Treat" or "treatment" or "treating" mean to lessen, eliminate, inhibit, improve, alter, or prevent a disease or condition, for example by administration of an estrogen receptor modulator or a SERM.

"Estrogen receptor mediated diseases or conditions" include any biological or medical disorder in which estrogen receptor activity is implicated or in which the inhibition of estrogen receptor potentiates or retards signaling through a pathway that is characteristically defective in the disease to be treated. The condition or disorder may either be caused or characterized by abnormal estrogen receptor activity. Representative estrogen receptor-mediated disorders include, for example, osteoporosis, atherosclerosis, estrogen-mediated cancers (e.g., breast and endometrial cancer), Turner's syndrome, benign prostate hyperplasia (i.e., prostate enlargement), prostate cancer, elevated cholesterol, restenosis, endometriosis, uterine fribroid disease, skin and/or vagina atrophy, Alzheimer's disease, androgenic alopecia, pregnancy, and pre- and post-menopausal associated conditions (e.g. libido, dryness, skin integrity, youthfulness, hot flashes, and the like). Successful treatment of a subject in accordance with the invention may result in the prevention, inducement of a reduction in, or alleviation of symptoms in a subject afflicted with an estrogen receptor-mediated medical or biological disorder. Thus, for example, treatment can result in a reduction in breast or endometrial tumors and/or various clinical markers associated with such cancers. Likewise, treatment of Alzheimer's disease can result in a reduction in rate of disease progression, detected, for example, by measuring a reduction in the rate of increase of dementia.

"Alkyl" means aliphatic hydrocarbon group which may be branched or straight-chained having about 1 to about 10 carbon atoms. Preferred alkyl is "lower alkyl" having about 1 to about 3 carbon atoms; more preferred is methyl. Branched means that one or more lower alkyl groups such as methyl, ethyl, or propyl are attached to a linear alkyl chain.

"Prodrug" means a form of the compound of formula I suitable for administration to a patient without undue toxicity, irritation, allergic response, and the like, and effective for their intended use. A prodrug is transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, et., Bioreversible Carriers in Drug Design, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are H$_2$O.

It will be appreciated by those skilled in the art that compounds used in the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase). It is also well known in the art and, for example, as illustrated hereinbelow how to determine estrogen receptor activity using the standard tests described herein, or using other similar tests.

One embodiment of the present invention is a method for preventing, diagnosing, or treating a condition mediated by an estrogen receptor by administering to a patient in need thereof an effective amount of a compound of formula I, II, or a combination thereof:

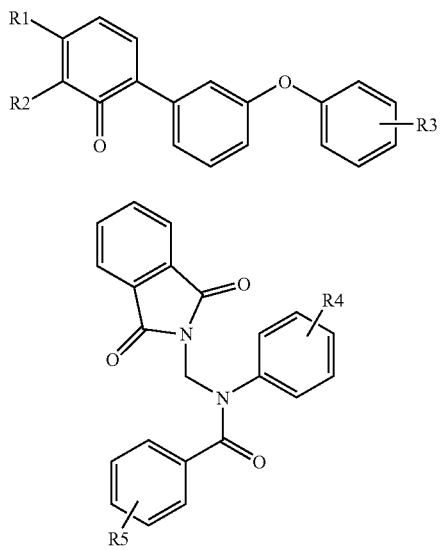

wherein R1, R3, and R4 are independently selected from H, OH, and $OR_a$;

R2 is selected from H, OH, and $(C\!=\!O)(C_{1-7})$alkyl;

R5 is H or OH;

$R_a$ is $(C_{1-7})$alkyl or $(C\!=\!O)(C_{1-7})$alkyl or a derivative of the compound selected from N-oxide derivatives, prodrug derivatives, protected derivatives, isomers, and mixtures of isomers of the compound; or a pharmaceutically acceptable salt or solvate of the compound or the derivative.

Preferably, $R_a$ is $CH_3$ or $(C\!=\!O)CH_3$.

Preferred configurations of formula I are set forth in Table 1:

TABLE 1

| R1 | R2 | R3 |
|---|---|---|
| OH | $(C\!=\!O)CH_2CH_3$ | H |
| OH | $(C\!=\!O)CH_2CH_3$ | OH |
| OH | OH | OH |
| OH | H | H |
| OH | H | OH |
| H | OH | H |
| H | OH | OH |
| H | H | H |
| H | H | OH |
| $OR_a$ | H | H |
| $OR_a$ | H | OH |
| $OR_a$ | OH | OH |
| $OR_a$ | H | $OR_a$ |
| H | H | $OR_a$ |
| OH | H | $OR_a$ |

The compound wherein R1 is OH, R2 is $(C\!=\!O)CH_2CH_3$, and R3 is H is referred to herein as "Compound A" or "MS__1105" (Bionet Research, Cornwall, England).

Preferred configurations of formula II are set forth in Table 2:

TABLE 2

| R4 | R5 |
|---|---|
| OH | H |
| OH | OH |
| H | OH |
| $OR_a$ | H |
| $OR_a$ | OH |

The compound wherein R4 is OH and R5 is H is referred to herein as "Compound B" or "3257-4404" (ChemDiv, Inc., San Diego, Calif.).

In one embodiment, the estrogen mediated condition is selected from osteoporosis, atheroschlerosis, estrogen-mediated cancers (e.g. breast cancer or endometrial cancer), Turner's syndrome, benign prostate hyperplasia, prostate cancer, elevated cholesterol, restenosis, endometriosis, uterine fribroid disease, skin and/or vagina atrophy, Alzheimer's disease, androgenic alopecia, pregnancy, and pre- and postmenopausal associated conditions (e.g. libido, dryness, skin integrity, youthfulness, hot flashes, and the like).

Yet another embodiment includes administering a compound of formula I or II to a patient in need thereof in a preventative or prophylactic amount. The need for a prophylactic administration according to the methods of the present invention is determined via the use of well known risk factors. The effective amount of an individual compound is determined, in the final analysis, by the physician in charge of the case, but depends on factors such as the exact estrogen mediated condition or disease to be treated, the severity of the condition or disease and other conditions or diseases from which the patient suffers, the chosen route of administration other drugs and treatments which the patient may concomitantly require, and other factors in the physician's judgment.

Another embodiment includes an in vitro method for diagnosing a disease or condition in a patient as estrogen receptor-mediated by exposing a sample (e.g. cancer cells) from the patient to a labeled compound of formula I or II under conditions such that the labeled compound can bind to an estrogen receptor present in the sample. Suitable labels for the compound are readily determinable by one of skill in the art and include, for example, radio-labels, fluorescent labels, luminescent labels, and the like. The amount of estrogen receptor-bound compound present in the sample can be determined by detecting and quantifying the signal from the bound label.

The compounds used in the methods of the present invention may be prepared by employing procedures known in the literature starting from known compounds or readily prepared intermediates. Compounds can also be obtained from commercial suppliers, for example, Asinex Corp. (Winston-Salem, N.C.), Bionet Research (Cornwall, England), Sigma (St. Louis, Mo.), Maybridge (Geel, Belgium), and ChemDiv, Inc. (San Diego, Calif.).

In practice, a composition containing a compound of formula I or II may be administered in any variety of suitable forms, for example, by inhalation, topically, parenterally, rectally, or orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

A composition containing a compound of formula I or II may be presented in forms permitting administration by the most suitable route. The invention also relates to administering compositions containing a compound of formula I or II which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions.

The choice of vehicle and the compound of formula I or II in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the compound of formula I or II may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the compound of formula I or II as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the compound of formula I or II in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing the compound of formula I or II may be used. The compound of formula I or II may be also incorporated in a gel or matrix base for application in a patch, which would allow a controlled release of compound through transdermal barrier.

For administration by inhalation, the compound of formula I or II may be dissolved or suspended in a suitable carrier for use in a nebulizer or a suspension or solution aerosol, or may be absorbed or adsorbed onto a suitable solid carrier for use in a dry powder inhaler.

Compositions according to the invention may also be formulated in a manner which resists rapid clearance from the vascular (arterial or venous) wall by convection and/or diffusion, thereby increasing the residence time of the particles at the desired site of action. A periadventitial depot comprising a compound according to the invention may be used for sustained release. One such useful depot for administering a compound according to the invention may be a copolymer matrix, such as ethylene-vinyl acetate, or a polyvinyl alcohol gel surrounded by a Silastic shell. Alternatively, a compound according to the invention may be delivered locally from a silicone polymer implanted in the adventitia.

An alternative approach for minimizing washout of a compound according to the invention during percutaneous, transvascular delivery comprises the use of nondiffusible, drug-eluting microparticles. The microparticles may be comprised of a variety of synthetic polymers, such as polylactide for example, or natural substances, including proteins or polysaccharides. Such microparticles enable strategic manipulation of variables including total dose of drug and kinetics of its release. Microparticles can be injected efficiently into the arterial or venous wall through a porous balloon catheter or a balloon over stent, and are retained in the vascular wall and the periadventitial tissue for at least about two weeks. Formulations and methodologies for local, intravascular site-specific delivery of therapeutic agents are discussed in Reissen et al. (Am. C'oll. Cardial. 1994; 23: 1234-1244), the entire contents of which are hereby incorporated by reference.

A composition according to the invention may also comprise a hydrogel which is prepared from any biocompatible or non-cytotoxic (homo or hetero) polymer, such as a hydrophilic polyacrylic acid polymer that can act as a drug absorbing sponge. Such polymers have been described, for example, in application WO93/08845, the entire contents of which are hereby incorporated by reference. Certain of them, such as, in particular, those obtained from ethylene and/or propylene oxide are commercially available.

For the treatment of restenosis, the compounds of the invention are administered directly to the blood vessel wall by means of an angioplasty balloon, which is coated with a hydrophilic film (for example a hydrogel) which is saturated with the compound, or by means of any other catheter containing an infusion chamber for the compound, which can thus be applied in a precise manner to the site to be treated and allow the compound to be liberated locally and efficiently at the location of the cells to be treated. This method of administration advantageously makes it possible for the compound to contact quickly the cells in need of treatment.

The treatment method of the invention preferably consists in introducing a compound according to the invention at the site to be treated. For example, a hydrogel containing composition can be deposited directly onto the surface of the tissue to be treated, for example during a surgical intervention.

Advantageously, the hydrogel is introduced at the desired intravascular site by coating a catheter, for example a balloon catheter, and delivery to the vascular wall, preferably at the time of angioplasty. In a particularly advantageous manner, the saturated hydrogel is introduced at the site to be treated by means of a balloon catheter. The balloon may be chaperoned by a protective sheath as the catheter is advanced toward the target vessel, in order to minimize drug washoff after the catheter is introduced into the bloodstream.

Another embodiment of the invention provides for a compound according to the invention to be administered by means of perfusion balloons. These perfusion balloons, which make it possible to maintain a blood flow and thus to decrease the risks of ischaemia of the myocardium, on inflation of the balloon, also enable the compound to be delivered locally at normal pressure for a relatively long time, more than twenty minutes, which may be necessary for its optimal action. Alternatively, a channeled balloon catheter ("channeled balloon angioplasty catheter", Mansfield Medical, Boston Scientific Corp., Watertown, Mass.) may be used. The latter consists of a conventional balloon covered with a layer of 24 perforated channels, which perfuse via an independent lumen through an additional infusion orifice.

Various types of balloon catheters, such as double balloon, porous balloon, microporous balloon, channel balloon, balloon over stent and hydrogel catheter, all of which may be used to practice the invention, are disclosed in Reissen et al. (1994), the entire contents of which are hereby incorporated by reference.

The use of a perfusion balloon catheter is especially advantageous, as it has the advantages of both keeping the balloon inflated for a longer period of time by retaining the properties of facilitated sliding and of site-specificity of the hydrogel are gained simultaneously.

Another aspect of the present invention relates to a pharmaceutical composition comprising a compound of formula I or II and poloxamer, such as Poloxamer 407, a non-toxic, biocompatible polyol, commercially available (BASF, Parsippany, N.J.).

A poloxamer impregnated with a compound of formula I or II may be deposited directly on the surface of the tissue to be treated, for example during a surgical intervention. Poloxamer possesses essentially the same advantages as hydrogel while having a lower viscosity.

The use of a channel balloon catheter with a poloxamer impregnated with a compound of formula I or II is especially advantageous. In this case, the advantages of both keeping the balloon inflated for a longer period of time while retaining the properties of facilitated sliding, and of site specificity of the poloxamer, are gained simultaneously.

In another embodiment, the compound of formula I or II is administered as a properly formulated coating on a stent device. Examples of stent devices to which a SERM has been applied are disclosed in U.S. Pat. No. 6,471,979, the contents of which are incorporated herein by reference.

In one aspect, the coating on a stent device is formed by applying polymeric material in which the compound of formula I or II is incorporated to at least one surface of the stent device.

Polymeric materials suitable for incorporating the compound of formula I or II include polymers having relatively low processing temperatures such as polycaprolactone, poly (ethylene-co-vinyl acetate) or poly (vinyl acetate or silicone gum rubber and polymers having similar relatively low processing temperatures. Other suitable polymers include non-degradable polymers capable of carrying and delivering therapeutic drugs such as latexes, urethanes, polysiloxanes, styrene-ethylene/butylene-styrene block copolymers (SEBS) and biodegradable, bioabsorbable polymers capable of carrying and delivering therapeutic drugs, such as poly-DL-lactic acid (DL-PLA), and poly-L-lactic acid (L-PLA), polyolthoesters, polyiminocarbonates, aliphatic polycarbonates, and polyphosphazenes.

A porosigen may also be incorporated in the drug-loaded polymer by adding the porosigen to the polymer along with the therapeutic drug to form a porous drug-loaded polymeric membrane.

"Porosigen" means as any moiety, such as microgranules of sodium chloride, lactose, or sodium heparin, for example, which will dissolve or otherwise be degraded when immersed in body fluids to leave behind a porous network in the polymeric material. The pores left by such porosigens can typically be as large as 10 microns. The pores formed by porosigens such as polyethylene glycol (PEG), polyethylene oxide/polypropylene oxide (PEO/PPO) copolymers, for example, can also be smaller than one micron, although other similar materials which form phase separations from the continuous drug loaded polymeric matrix and can later be leached out by body fluids can also be suitable for forming pores smaller than one micron. The polymeric material can be applied to the stent while the therapeutic drug and porosigen material are contained within the polymeric material, to allow the porosigen to be dissolved or degraded by body fluids when the stent is placed in a blood vessel, or alternatively, the porosigen can be dissolved and removed from the polymeric material to form pores in the polymeric material prior to placement of the polymeric material combined with the stent within a blood vessel.

If desired, a rate-controlling membrane can also be applied over the drug loaded polymer, to limit the release rate of the compound of the invention. The rate-controlling membrane can be added by applying a coating form a solution, or a lamination. The rate-controlling membrane applied over the polymeric material can be formed to include a uniform dispersion of a porosigen in the rate-controlling membrane, and the porosigen in the rate-controlling membrane can be dissolved to leave pores in the rate-controlling membrane typically as large as 10 microns, or as small as 1 micron, for example, although the pores can also be smaller than 1 micron. The porosigen in the rate-controlling membrane can be, for example sodium chloride, lactose, sodium heparin, polyethylene glycol, polyethylene oxide/polypropylene oxide copolymers, or mixtures thereof.

In another aspect, the coating on the stent device can be formed by applying the compound of formula I or II to at least one surface of the stent device to form a bioactive layer and then applying one or more coats of porous polymeric material over the bioactive layer, such that the porous polymeric material has a thickness adequate to provide a controlled release of the compound.

In one aspect, the porous polymeric material is composed of a polyamide, parylene or a parylene derivative applied by catalyst-free vapor desposition. "Parylene" refers to a polymer based on p-xylylene and made by vapor phase polymerization as described in U.S. Pat. No. 5,824,049, incorporated herein by reference.

Alternatively, the porous polymeric material is applied by plasma deposition. Representative polymers suitable for plasma deposition include poly (ethylene oxide), poly (ethylene glycol), poly (propylene oxide), and polymers of methane, silicone, tetrafluoroethylene tetramethyldisiloxane, and the like.

Other suitable polymer systems include polymers derived from photopolymerizable monomers such as liquid monomers preferably having at least two cross linkable C—C (Carbon to Carbon) double bonds, and being a non-gaseous addition polymerizable ethylenically unsaturated compound, having a boiling point above 100° C., at atmospheric pressure, a molecular weight of about 100-1500 and being capable of forming high molecular weight addition polymers readily. More preferably, the monomer is preferably an addition photopolymerizable polyethylenically unsaturated acrylic or methacrylic acid ester containing two or more acrylate or methacrylate groups per molecule or mixtures thereof.

Representative examples of such multifunctional acrylates are ethylene glycol diacrylate, ethylene glycol dimethacrylate, trimethylopropane triacrylate, trimethylopropane trimethacrylate, pentaerythritol tetraacrylate, or pentaerythritol tetramethacrylate. 1 amides of (meth) acrylic acid, such as N-methylol methacrylamide butyl ether are also suitable, N-vinyl compounds such as N-vinyl pyrrolidone, vinyl esters of aliphatic monocarboxylic acids such as vinyl oleate, vinyl ethers of diols such as butanediol-1,4-divinyl ether and allyl ether and allyl ester are also suitable. Also included are other monomers such as the reaction products of di- or polyepoxides such as butanediol-1,4-diglycidyl ether or bisphenol A diglycidyl ether with (meth) acrylic acid. The characteristics of the photopolymerizable liquid dispersing medium can be modified for the specific purpose by a suitable selection of monomers or mixtures thereof.

Other useful polymer systems include a polymer that is biocompatible and minimizes irritation to the vessel wall when the stent is implanted. The polymer may be either a biostable or a bioabsorbable polymer depending on the desired rate of release or the desired degree of polymer stability. Bioabsorbable polymers that could be used include poly (L-lactic acid), polycaprolactone, poly (lactide-co-glycolide), poly (hydroxybutyrate), poly (hydroxybutyrate-co-valerate), polydioxanone, polyorthoester, polyanhydride, poly (glycolic acid), poly (D, L-lactic acid), poly (glycolic acidcotrimethylene carbonate), polyphosphoester, polyphosphoester urethane, poly (amino acids), cyanoacrylates, poly (trimethylene carbonate), poly (iminocarbonate), copoly (ether-esters) (e.g., PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefine copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones, polyvinyl aromatics, such as polystyrene, polyvinyl esters, such as polyvinyl acetate; copolymers of vinyl monomers with each other and olefins, such as ethylene-methyl methacrylate copolymers, acrylonitril-styrene copolymers, ABS resins, and ethylene-vinyl acetate copolymers; polyamides, such as Nylon 66 and polycaprolactam; alkyl reins, polycarbonates; polyoxymethylenes; polyimides, polyethers; epoxy reins, polyurethanes; rayon; rayon-triacetate; cellulose, cellulose acetate, cellulose butyrate; cellulose acetate butyrate; cellophane, cellulose nitrate; cellulose propionate; cellulose ethers; and carboxymethyl cellulose.

In addition to plasma deposition and vapor phase deposition, other techniques for applying the various coatings on the stent surfaces may be employed. For example, a polymer solution may be applied to the stent and the solvent allowed to evaporate, thereby leaving on the stent surface a coating of the polymer and the therapeutic substance. Typically, the solution can be applied to the stent by either spraying the solution onto the stent or immersing the stent in the solution.

The compound of formula I or II may be used in the treatment of restenosis in combination with any anticoagulant, antiplatelet, antithrombotic or profibrinolytic agent. Often patients are concurrently treated prior, during and after interventional procedures with agents of these classes either in order to safely perform the interventional procedure or to prevent deleterious effects of thrombus formation. Some examples of classes of agents known to be anticoagulant, antiplatelet, antithrombotic or profibrinolytic agents include any formulation of heparin, low molecular weight heparins, pentasaccharides, fibrinogen receptor antagonists, thrombin inhibitors, Factor Xa inhibitors, or Factor VIIa inhibitors.

The percentage of compound of formula I or II in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound of formula I or II.

The compound of formula I or II used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the compound of formula I or II may be administered 1 to 4 times per day. Of course, for other patients, it will be necessary to prescribe not more than one or two doses per day.

The following non-limiting examples set forth hereinbelow illustrate certain aspects of the invention.

EXAMPLES

Employing computational ("in silico") screening of databases of commercially available chemicals, previously unrecognized estrogenic compounds were identified. Biological assays indicated that two of these compounds:

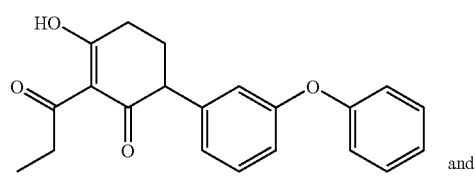

(Compound A)

and

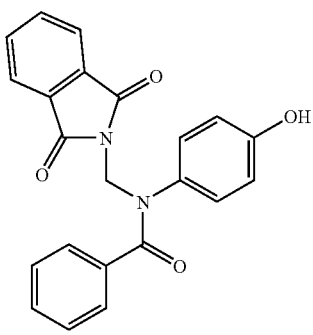

(Compound B)

are strong estrogen receptor (ER) antagonists. Subsequent computer-aided molecular modeling studies, in which these two compounds were "docked" inside the estrogen binding pocket of ER, elucidated their mode of ER binding.

The ER antagonist 4-hydroxy (4-OH) tamoxifen and ER agonist diethylstilbestrol (DES) were selected as queries to search a virtual (i.e., computer accessible) database of ~200,000 commercially available compounds. Both molecules possess high binding affinity for the ERα comparable in strength to the endogenous hormone 17β-estradiol, and together they represent archetypical examples of ER ligands.

Numerous "hits" were identified including, as expected, known estrogenic compounds. After elimination of the hits already reported as estrogenic, nine compounds were selected for further experimental validation of their estrogenic activity.

To assay each of the selected hits from the search, a 25 μM sample was tested using the NR peptide ERα ELISA kit (Active Motif, Carlsbad, Calif.) according to manufacturer's instructions. Relative units of light intensity for each test compound were normalized to the vehicle control (DMSO) and then expressed in percentage of ER activation. Compounds exhibiting over 100% ER activation were identified as agonists, and below 100% as antagonists based on profiles of positive (17β-estradiol) and negative (tamoxifen) controls (FIG. 1). The data reported here represent results of three independent determinations in duplicate. Error bars represent the standard deviation of the three determinations. All compounds were dissolved in DMSO as vehicle control with final concentration of less than 2.5% of DMSO.

Of the nine test compounds, several exhibited appreciable ER antagonist activity as compared with vehicle control (100% ER activation) and tamoxifen (35.7%): mifepristone (51.7%), Compound A (53.1%), and Compound B (69%). Compounds 5386105 and 8R-0263 exhibited weak antagonist activity (82.1% and 77.9%). Compared with the strong agonists DES (178.6%) and 17β-estradiol (148.5%), the test compound 4-hydroxy estradiol (196.3%) exceptional potency. We later discovered that this compound was previously shown as estrogenic, consistent with our in silico prediction. The remaining three test compounds (8R-0263, ASN_3780064, and SP-00944) showed only marginal estrogenic activity.

Mifepristone (RU486), the biologically active agent in the so-called "morning-after pill", has been reported as a progesterone (PR) and glucocorticoid receptor (GR) antagonist. Although mifepristone has been shown to bind PR and GR directly, its ability to bind ER has not been previously reported to our knowledge. This unexpected finding of strong ER binding by mifepristone could be due to the presence of both ER and PR in the MCF-7 nuclear extract. The similarity of the ligand binding domains (LBDs) of ER and PR might preclude discrimination by the ELISA-based assay. Subsequent competitive binding assays were conducted to explore this possibility.

A gel filtration displacement assay for estrogen receptor alpha (ERα) was employed to assess competitive binding by ER antagonists among the test compounds in 10 μM. ER binding assays were conducted in duplicate in 50 mM Tris-HCl, pH7.5, 1 mM EDTA, 20% Glycerol and 1 mM DTT buffer. Radioligands that were used include [6, 7-$^3$H] estradiol (specific activity 44 Ci/mmol, Amersham Biosciences). Binding assays were conducted on ice in a volume of 1 mL with 10 ng of purified full-length ERα (Active Motif, Carlsbad, Calif.) and 25 nM 3H-estradiol in final concentration; 10 μM 17β-Estradiol and 4-OH tamoxifen (Sigma) were used to define positive displacements as competing ligands respectively.

Figure 2:
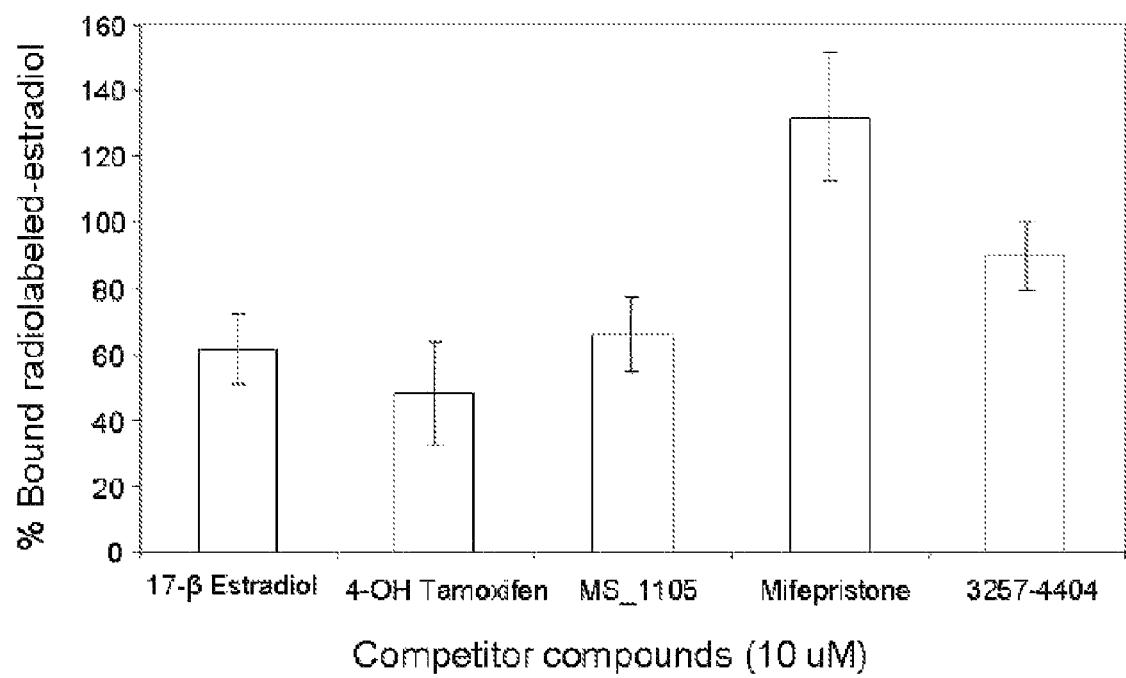
FIG. 2 illustrates the results of ER competitive binding assays of the three lead antagonists.

Following 1-hour incubation, assays were terminated by filtration through Whatman GF/B filters. Filters were soaked in Ecoscint liquid scintillation mixture (National Diagnostics, Somerville, N.J.) and filter-bound radioactivity was counted using a Beckman LS 1071 counter. Counts were normalized to the negative controls (no cold ligand) as the percentage of bound radiolabeled-estradiol remaining after separating bound radioligand from free radioligand. The negative controls were taken as 100% bound radioligand remaining. The lower the percentage of bound radiolabeled-estradiol implies a stronger binding affinity by the test compound as definitive evidence of true ER ligands. Results are reported as the average values of three independent experiments in duplicate. Error bars represent standard deviation of the three determinations (FIG. 2).

The >100% retention of radiolabeled-estradiol upon addition of mifepristone indicated that mifepristone, a well-known ligand of the PR and GR, does not bind to ER directly. Instead, mifepristone exerts its anti-estrogenic activity indirectly through an ER-independent pathway. Since MCF-7 nuclear extract was used as the source for ER, the ELISA kit could have captured PR instead of ER when treated with mifepristone because of the similarity between the LBDs of ER and PR.

Two remaining antagonists (Compound A and Compound B) were confirmed as true ligands of ERα. Both showed significant radioligand displacement of ERα with 65.9% and 89.8% bound radioligand remaining, respectively (FIG. 2). The positive controls, 17β-estradiol or 4-OH tamoxifen, were determined to have 61.5% and 48.1% bound radiolabeled-estradiol remaining respectively (FIG. 2). The present results indicate that the ER affinity is higher for Compound A than for Compound B. In fact, Compound A is comparable to the positive controls (known ligands with high affinity to ER) in terms of percentage of displaced radioligand.

Figure 3:
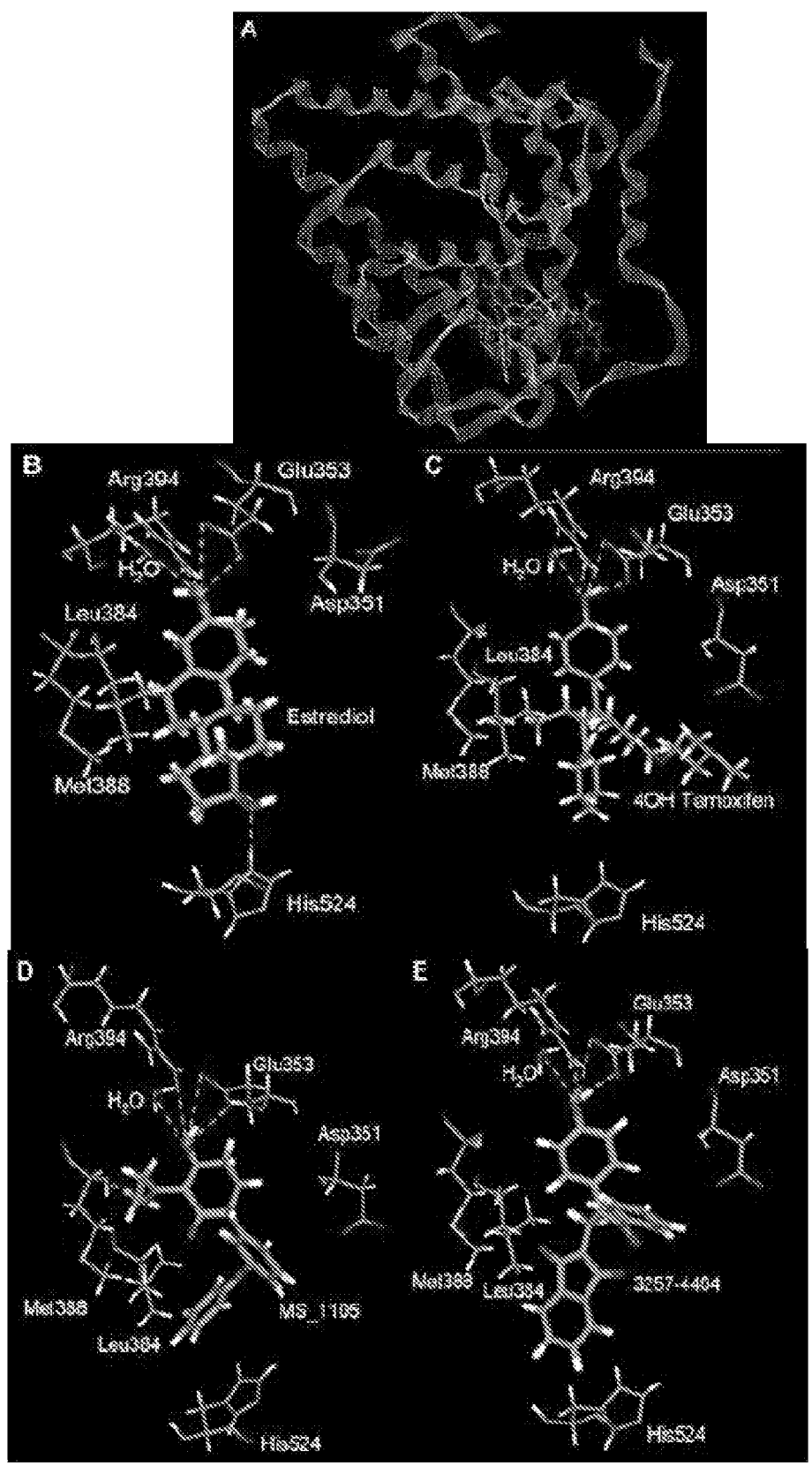
FIG. 3 is a molecular modeling study of ER-ligand complex; (A) human ER LBD is represented by white ribbon lines and the ligands 4-OH Tamoxifen, raloxifene, Compound B, and Compound A are shown in capped stick representation; (B)-(E) hydrogen bonds are represented as dashed lines between residues of the binding pocket of ER LBD and the following ligands: 17β-estradiol (B), 4-hydroxy tamoxifen (C), Compound A (D), and Compound B (E).

Molecular modeling studies were conducted on Compound A and Compound B after docking them inside the binding pocket of the ER LBD. The primary objectives were to glean insights about their relative binding affinities and functional effects as antagonists. This was achieved by comparing their binding poses with 17 β-estradiol and 4-OH tamoxifen as they appear in complex with the ER LBD x-ray crystal structures (1GWR and 3ERT, respectively). Visual inspection of Compound A and Compound B immediately revealed that they adopt an extended conformation spanning ~12 Å that is characteristic of high-affinity ER ligands such as 17β-estradiol and 4-OH tamoxifen (FIG. 3).

The competitive binding assays yielded the following order in terms of binding affinity: 17 β-estradiol≧4-OH tamoxifen≧Compound A>Compound B. Examination of the hydrogen bonding interactions for these ER ligands revealed a consistent pattern (FIG. 3). Specifically, hydrogen bonds are evident with the sidechains of three residues (Glu353, Arg394, and His524) for the strong agonist 17β-estradiol and two residues (Glu353 and Arg394) for the strong antagonist 4-OH tamoxifen. The Arg sidechain, which contains the protonated guanidinium group, can participate in multiple stable hydrogen bonds concurrently. Compound A forms a hydrogen bond with the sidechain of Glu353, but the key interaction with Arg394 is replaced by a weaker hydrogen bond with the backbone NH of Met388. Compound B forms a single hydrogen bond, with Glu353. In summary, the weaker ER binding affinities of Compound A and Compound B compared with 4-OH tamoxifen may be explained in terms of the disparity in strength (for Compound A) and number (for Compound B) of their hydrogen bonds.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A method for diagnosing or treating a condition mediated by an estrogen receptor, said method comprising administering to a patient in need thereof an effective amount of a compound of formula I, II, or a combination thereof:

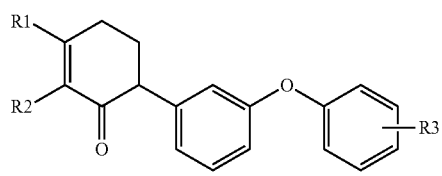

(I)

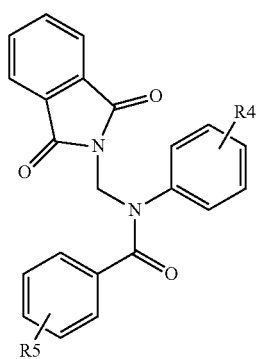

(II)

wherein R1, R3, R4, and R5 are independently selected from the group consisting of H, OH, and $OR_a$;
R2 is selected from the group consisting of H, OH, and (C=O)($C_{1-7}$)alkyl;
$R_a$, is ($C_{1-7}$)alkyl or (C=O)($C_{1-7}$)alkyl; or
a derivative of said compound selected from the group consisting of N-oxide derivatives, prodrugs, isomers, and mixtures of isomers of said compound; or a pharmaceutically acceptable salt or solvate of said compound or said derivative.

2. The method of claim 1, wherein R1 is OH, R2 is (C=O)$CH_2CH_3$, and R3 is H.

3. The method of claim 1, wherein R4 is OH and R5 is H.

4. The method of claim 1, wherein said condition is selected from the group consisting of osteoporosis, atheroschlerosis, estrogen-mediated cancers, Tumer's syndrome, benign prostate hyperplasia, prostate cancer, elevated cholesterol, restenosis, endometriosis, uterine fribroid disease, skin and/or vagina atrophy, Alzheimer's disease, androgenic alopecia, pregnancy, and pre- and post-menopausal associated conditions.

5. The method of claim 1, wherein said estrogen-mediated cancer is breast cancer or endometrial cancer.

6. A compound of formula I or II:

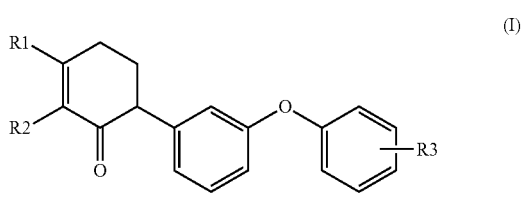

(I)

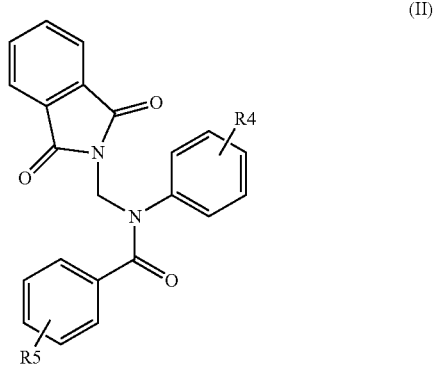

(II)

wherein R1, R3, R4, and R5 are independently selected from the group consisting of H, OH, and $OR_a$;
R2 is selected from the group consisting of H, OH, and (C=O)($C_{1-7}$)alkyl;
Ra is ($C_{1-7}$)alkyl or (C=O)($C_{1-7}$)alkyl; or
a derivative of said compound selected from the group consisting of N-oxide derivatives, prodrugs, isomers, and mixtures of isomers of said compound; or a pharmaceutically acceptable salt or solvate of said compound or said derivative;
provided that R3 is OH or $OR_a$ when R1 is OH and R2 is (C=O)$CH_2CH_3$; and
R4 is H or $OR_a$, when R5 is H.

7. A pharmaceutical composition comprising an effective amount of the compound of claim 6 and a pharmaceutically acceptable carrier.

8. A method for diagnosing a condition in a patient as an estrogen receptor-mediated condition comprising (a) exposing a sample from the patient affected by the condition to a labeled compound of formula I or II:

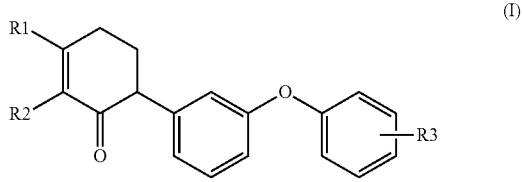

(I)

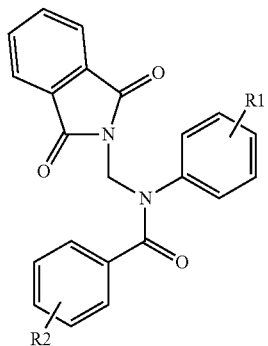

(II)

wherein R1, R3, R4, and R5 are independently selected from the group consisting of H, OH, and $OR_a$;

R2 is selected from the group consisting of H, OH, and (C=O)($C_{1-7}$)alkyl;

Ra is ($C_{1-7}$)alkyl or (C=O)($C_{1-7}$)alkyl; or a derivative of said compound selected from the group consisting of N-oxide derivatives, prodrugs, isomers, and mixtures of isomers of said compound; or a pharmaceutically acceptable salt or solvate of said compound or said derivative;

provided that R3 is OH or $OR_a$ when R1 is OH and R2 is (C=O)$CH_2CH_3$; and

R4 is H or $OR_a$, when R5 is H;

under conditions such that the labeled compound can bind to an estrogen receptor present in the sample and (b) detecting a signal from the labeled compound bound to the estrogen receptor.

* * * * *